United States Patent
Seo et al.

(10) Patent No.: US 11,332,710 B2
(45) Date of Patent: May 17, 2022

(54) **METHOD FOR PREPARING FERMENTED SOY PRODUCT USING *BACILLUS AMYLOLIQUEFACIENS***

(71) Applicant: CJ CHEILJEDANG CORPORATION, Seoul (KR)

(72) Inventors: Hyojeong Seo, Seoul (KR); Bina Kim, Seoul (KR); Jungeun Kim, Seoul (KR); Seong Bo Kim, Seoul (KR); Seung Won Park, Seoul (KR); Youngho Hong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 11 days.

(21) Appl. No.: 16/641,899

(22) PCT Filed: Aug. 30, 2018

(86) PCT No.: PCT/KR2018/010074
§ 371 (c)(1),
(2) Date: Feb. 25, 2020

(87) PCT Pub. No.: WO2019/045493
PCT Pub. Date: Mar. 7, 2019

(65) Prior Publication Data
US 2020/0199691 A1    Jun. 25, 2020

(30) Foreign Application Priority Data

Aug. 31, 2017 (KR) .................. 10-2017-0111472
May 14, 2018 (KR) .................. 10-2018-0054965

(51) Int. Cl.
| | | |
|---|---|---|
| *A61K 36/48* | (2006.01) | |
| *C12N 1/20* | (2006.01) | |
| *A23K 10/18* | (2016.01) | |
| *A23K 10/30* | (2016.01) | |
| *C12R 1/07* | (2006.01) | |

(52) U.S. Cl.
CPC .............. *C12N 1/205* (2021.05); *A23K 10/18* (2016.05); *A23K 10/30* (2016.05); *C12R 2001/07* (2021.05)

(58) Field of Classification Search
None
See application file for complete search history.

(56) References Cited

U.S. PATENT DOCUMENTS

| | | | | |
|---|---|---|---|---|
| 10,874,118 B2 * | 12/2020 | Kim | .................. | C12N 1/20 |
| 2008/0292752 A1 * | 11/2008 | Song | .................. | A23L 11/33 |
| | | | | 426/46 |
| 2015/0147303 A1 | 5/2015 | Hsieh | | |
| 2016/0186273 A1 | 6/2016 | Taghavi et al. | | |

FOREIGN PATENT DOCUMENTS

| | | |
|---|---|---|
| EP | 3 101 136 A1 | 12/2016 |
| KR | 10-0459240 B1 | 11/2004 |
| KR | 10-0645284 B1 | 11/2006 |
| KR | 10-0925173 B1 | 10/2009 |
| KR | 10-1139027 B1 | 4/2012 |
| KR | 10-2014-0057436 A | 5/2014 |
| KR | 10-1517326 B1 | 4/2015 |
| KR | 10-1517326 * | 5/2015 |
| KR | 10-2016-0141267 A | 12/2016 |
| WO | 2014/069922 A1 | 5/2014 |

OTHER PUBLICATIONS

Lee, J. et al. Antimicrobial Activity of Bacillus amyloliquefaciens EMD17 . . . Food Science and Biotechnology 25(2)525-532, Apr. 2016. (Year: 2016).*
Li et al., "Transient Hypersensitivity to Soybean Meal in the Early-Weaned Pig," *J. Anim. Sci.* 68:1790-1799 (1990).
Xu et al., "Antibacterial activity of lipopeptides produced by *Bacillus amyloliquefaciens* M1 against multidrug-resistant *Vibrio* spp. Isolated from diseased marine animals," *Appl Microbiol Biotechnol* 98:127-136 (2014).

* cited by examiner

*Primary Examiner* — Ralph J Gitomer
(74) *Attorney, Agent, or Firm* — Seed IP Law Group LLP

(57) ABSTRACT

The present disclosure relates to a method for preparing a fermented soy product comprising: inoculating a *Bacillus amyloliquefaciens* CJ24-34 (KCCM12038P) strain into a soybean meal or a soy protein concentrate; and obtaining a fermented soybean meal or a fermented soy protein concentrate, which is fermented by culturing the *Bacillus amyloliquefaciens* strain, a fermented soy product prepared by the method, and an animal feed composition comprising the fermented product. The fermented soy product prepared by the method does not contain mucilage, shows an excellent antibacterial activity, and has a high content of low molecular weight peptides.

10 Claims, 3 Drawing Sheets

Specification includes a Sequence Listing.

[Fig. 1]
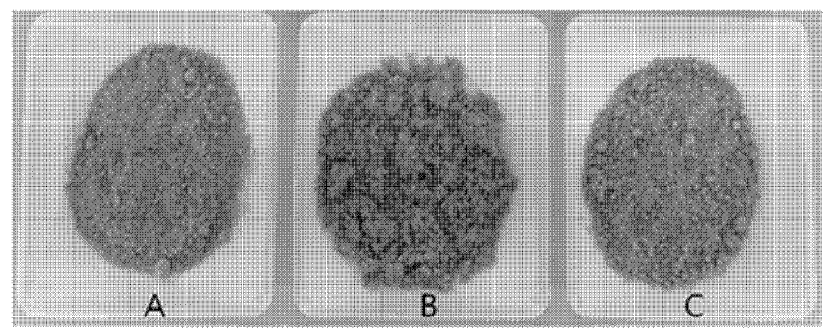
[Fig. 2]
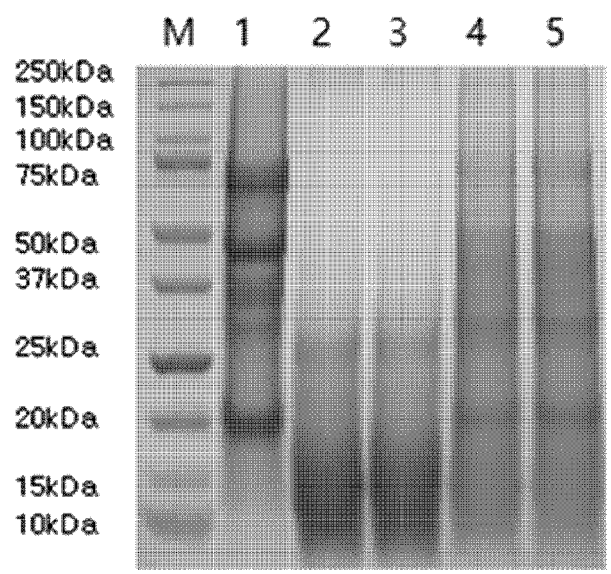
[Fig. 3]
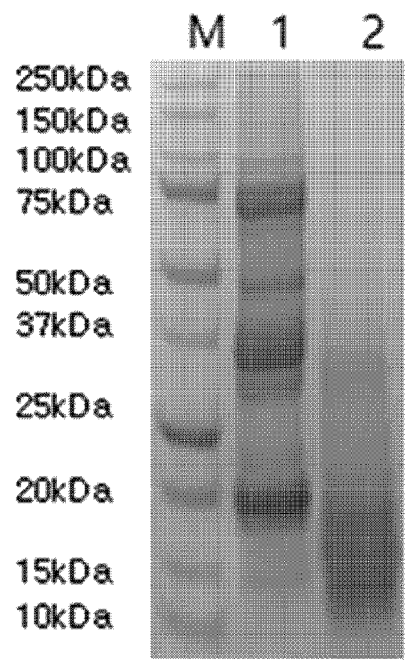

[Fig. 4]
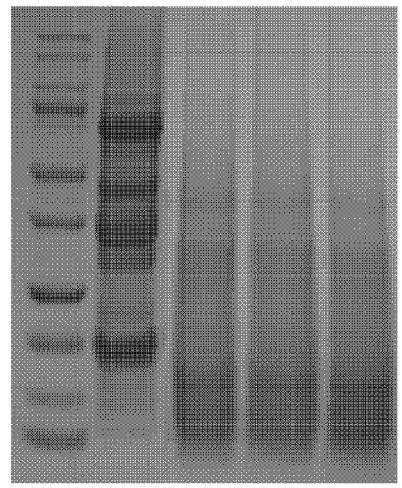

[Fig. 5]
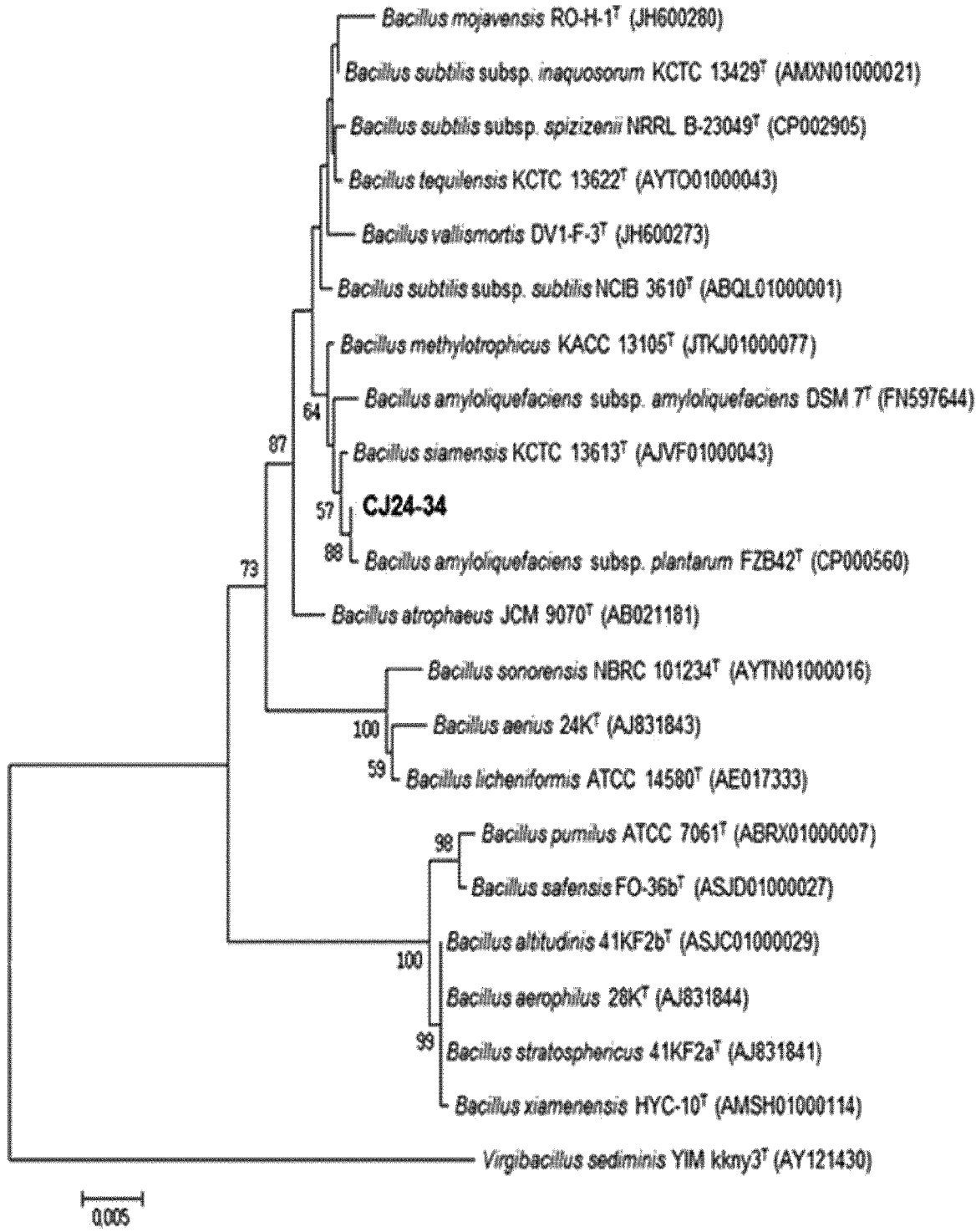

METHOD FOR PREPARING FERMENTED SOY PRODUCT USING *BACILLUS AMYLOLIQUEFACIENS*

TECHNICAL FIELD

The present disclosure relates to a novel *Bacillus amyloliquefaciens* CJ24-34 (KCCM12038P) strain and a method for preparing a fermented soy product using the same.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_466USPC_SEQUENCE_LISTING.txt. The text file is 3.5 KB, was created on Feb. 12, 2020, and is being submitted electronically via EFS-Web.

BACKGROUND ART

In general, animal feed contains fishmeal as a protein source, but the cost of fishmeal has been rising worldwide as the production thereof in fishmeal-producing countries has recently decreased, or the supply and demand of fishmeal have become unstable. Accordingly, there is an increasing demand for vegetable protein sources which can be used as a substitute for fishmeal, and efforts to develop the same are continuously underway. Typical vegetable proteins include proteins contained in nuts, beans and grains, but the soybean among soybean protein is known to be richer in proteins, fatty acids and polysaccharides than other soybeans.

Defatted soybean meal (hereinafter referred to as soybean meal) is a by-product remaining after extracting the fat from soybeans having high protein and fat contents. However, the soybean meal contains a variety of anti-nutritional factors (ANF), which can impair digestibility when used as a feed (Li et al., J. Anim Sci., 68:1790, 1990). In particular, a trypsin inhibitor (TI) is known to be a typical antioxidant that reduces protein utilization by inhibiting enzymatic activity in vivo. Especially, when the anti-nutritional factors are added to a feed for young livestock, the amount of use is restricted. In addition, the soybean protein is extracted from soybean meal using water or salt. These soy proteins can be classified into processed soy protein products of defatted soy flour, soy protein concentrates, structured soy proteins, hydrolyzed soy proteins, or soy protein isolates depending on the extent to which non-protein ingredients such as water-soluble and non-water-soluble carbohydrates are removed from the defatted soybean meal. In addition, because the soy proteins have a high protein content, they can be used for livestock feed, in addition to processed meat products, processed milk products, and foods such as bread or snacks.

However, the soy proteins extracted from soybean meals contain high molecular weight proteins consisting of protein subunits and many anti-nutritional factors (ANFs), which impair digestion, or the like. In particular, these anti-nutritional factors are known to impair the digestive ability of animals. Accordingly, in order to use soy proteins in animal feed, there is a need for research focusing on reducing anti-nutritional factors to increase the digestibility of animal feed and converting high molecular weight proteins into low molecular weight peptides.

Meanwhile, processed soy protein products such as soy protein concentrates, soy protein isolates, or hydrolyzed soy proteins, which are currently produced, are produced by chemical or enzymatic treatments. However, the chemical processing method imposes problems in that the production cost is high and that heat treatment, chemical treatment, heat drying, or the like in the course of the manufacturing process lead to protein denaturation and loss of water-soluble amino acids, which substantially decreases protein solubility. Because of this, the chemical processing method is subjected to heat treatment to an extent that extreme denaturation of proteins does not occur. Thus, a considerable amount of trypsin inhibitors, which are anti-nutritional factors, is present in the final soy protein product.

As a means of solving the problems of the chemical processing method of the processed soy protein products, a fermented soy product of a biological processing method for fermentation using *Bacillus* or fungi has been developed (Korean Patent Nos. 10-0645284, 10-0459240, 10-0925173, and 10-1139027). However, even for a fermented soybean meal or a fermented soy protein concentrate prepared by the biological processing method, the content of low molecular weight peptides and the content of the anti-nutritional factors in a processed product, which is related to the improvement of the digestibility, may vary depending on the species and strains of microorganism such as *Bacillus*, lactic acid bacteria, and yeast. In particular, even with the same species of microorganisms, the content may vary depending on the enzyme production capacity and growth rate of each strain (Korean Patent No. 10-1517326). That is, the strain used in the biological processing method is a crucial factor for indicating the difference in the characteristics and the digestibility of a final processed soy protein product.

Related prior art includes Korean Patent Nos. 10-0645284, 10-0459240, 10-0925173, and 10-1139027. According to the technique disclosed in the patents, it is true that a high-quality protein material for feed which has a high digestion-absorption rate can be implemented since many anti-nutritional factors can be removed during the fermentation process by using a seed culture of microorganism populations of *Bacillus subtilis, Aspergillus oryzae, Lactobacillus reuteri*, and *Saccharomyces cerevisiae*, and further a protein or carbohydrate can be decomposed into a low molecular weight peptide form. However, the microorganism populations, especially, *Bacillus subtilis* and *Bacillus amyloliquefaciens*, which are used for the fermentation of a soybean meal or a soybean protein concentrate, have the disadvantage of having low resistance to external contaminants and low protease-producing ability due to low antibacterial activity. In addition, some microbial strains produce mucilage during the fermentation process, and due to such mucilage, the permeability of the fermented product is deteriorated, thereby deteriorating the efficiency of aerobic fermentation.

Meanwhile, as prior art related to the present disclosure, the *Bacillus amyloliquefaciens* K2G strain disclosed by the applicant in Korean Patent No. 10-1517326 is capable of removing anti-nutritional factors, including trypsin inhibitors, has a high proteolytic ability and an antibacterial activity, and is useful for providing an animal feed containing low molecular weight peptides. However, the prior art references mentioned above neither disclose nor imply a novel strain having an antibacterial activity against various pathogenic microorganisms including *Salmonella, Vibrio*, and *Photobacterium* and capable of increasing the content of low molecular weight peptides and suppressing the production of mucilage, and a method for preparing a fermented soy product using the same.

PRIOR ART DOCUMENTS

Patent Documents (Patent Document 1) Korean Patent No. 10-0645284 (registered on Nov. 6, 2006)
(Patent Document 2) Korean Patent No. 10-0459240 (registered on Nov. 19, 2004)
(Patent Document 3) Korean Patent No. 10-0925173 (registered on Oct. 29, 2009)
(Patent Document 4) Korean Patent No. 10-1517326 (registered on Apr. 27, 2015)
(Patent Document 5) Korean Patent No. 10-1139027 (registered on Apr. 16, 2012)

Non-Patent Document (Non-Patent Document 1) Li et al., J. Anim Sci., 68:1790, 1990

DISCLOSURE OF INVENTION

Technical Problem

Under the circumstances, the present inventors have made extensive efforts to develop a method for preparing a fermented soy product of low molecular weight peptides by inoculating a novel *Bacillus amyloliquefaciens* CJ24-34 (KCCM12038P) strain into a soybean meal or a soy protein concentrate, and have developed a fermented soy product having an excellent antibacterial activity and no production of mucilage with an increased content of low molecular weight peptides, thereby completing the present disclosure.

Solution to Problem

One object of the present disclosure is to provide a method for preparing a fermented soy product of low molecular weight peptides by inoculating a novel *Bacillus amyloliquefaciens* CJ24-34 (KCCM12038P) strain into a soybean meal or a soy protein concentrate.

Another object of the present disclosure is to provide a novel *Bacillus amyloliquefaciens* CJ24-34 (KCCM12038P) strain, in which the content of low molecular weight peptides is increased and which has an excellent antibacterial activity and no production of mucilage.

Still another object of the present disclosure is to provide a fermented soy product prepared by the method above having an excellent antibacterial activity and no production of mucilage.

Further another object of the present disclosure is to provide an animal feed composition comprising the fermented soy product.

Other objects and advantages of the present disclosure will become apparent from the detailed description together with the appended claims and drawings. The contents not described in this specification can be sufficiently recognized and inferred by those skilled in the technical field or similar technical field of the present disclosure, and thus the description thereof will be omitted.

Advantageous Effects of Invention

The *Bacillus amyloliquefaciens* CJ24-34 strain according to the present disclosure has excellent antibacterial activity and proteolytic ability and has low mucilage-producing ability. Thus, a high-quality fermented soy product having a high content of low molecular weight peptides and an excellent antibacterial activity may be prepared by inoculating the strain into a soybean meal or soy protein concentrate. In particular, if the fermented soy product of the present disclosure is delivered to an animal susceptible for being exposed to various pathogenic bacteria, not only can the infection rate resulting from pathogenic bacteria be lowered and the survival rate increased due to its antibacterial activity, but also, the digestion-absorption rate can be enhanced due to a high content of low molecular weight peptides.

BRIEF DESCRIPTION OF DRAWINGS

FIG. 1 is a photograph showing the fermented soy protein concentrate.
FIG. 2 is a diagram showing SDS-PAGE results of the fermented soy protein concentrates.
FIG. 3 is a diagram showing SDS-PAGE results of the fermented soybean meal.
FIG. 4 is a diagram showing SDS-PAGE results of the fermented soybean meal under a low moisture condition.
FIG. 5 is a phylogenic tree showing the phylogenetic relationship of the novel *Bacillus amyloliquefaciens* CJ24-34 strain of the present disclosure.

BEST MODE FOR CARRYING OUT THE INVENTION

Each description and embodiment disclosed in the present disclosure can be applied to other descriptions and embodiments, respectively. That is, all combinations of various elements disclosed herein fall within the scope of the present disclosure. In addition, the scope of the present disclosure is not intended to be limited by the specific description described below.

In one aspect to achieve the objects above, the present disclosure provides a method for preparing a fermented soy product comprising: inoculating a *Bacillus amyloliquefaciens* CJ24-34 (KCCM12038P) strain into a soybean meal or a soy protein concentrate; and obtaining a fermented soybean meal or a fermented soy protein concentrate which is fermented by culturing the *Bacillus amyloliquefaciens* strain.

The *Bacillus amyloliquefaciens* CJ24-34 strain according to the present disclosure has an excellent protease activity and an excellent antibacterial activity against pathogens, and has reduced mucilage-producing ability during fermentation, and thus, a high-quality fermented soybean product can be produced.

As used herein, the term "fermented soy product" refers to a product, a fermented soy protein concentrate or a fermented soybean meal obtained by inoculating the strain of the present disclosure or a control strain into the soy protein concentrate or soybean meal.

As used herein, the term "soy protein concentrate" refers to a protein concentrate extracted from soybean, which is a legume. The protein extracted from soybean is produced by extracting soybean oil from soybean using an organic solvent such as hexane or the like and then removing non-protein ingredients such as water-soluble and non-water-soluble carbohydrates from a residual defatted soybean.

As used herein, the term "soybean meal" refers to a vegetable protein feed most commonly used as a product resulting from milking soybean, which is a legume. Soybean meal is the most economical and high-quality vegetable protein feed for animals and is a by-product produced while extracting oil from soybean.

As used herein, the term "*Bacillus amyloliquefaciens*", which is a microorganism in the genus *Bacillus*, is a gram-positive soil bacterium. It is known to have a close relationship with *Bacillus subtilis* and produces an antibiotic called barnase, a type of BamH1 enzyme and a ribonuclease. The soil bacteria are known as antibacterial active bacteria against the root infections of plants, especially in agriculture.

In recent years, the use of antibiotics has been limited in animal feed, and fermented soy products, which are vegetable proteins, are being used as a protein source. Therefore, the natural antibacterial properties of a feed composition, in particular, the antibacterial activity of the fermented soy products have become more important in terms of reducing the diseases caused by pathogenic microorganisms. Accordingly, the present inventors have made extensive efforts to develop a strain having an antibacterial activity against various pathogens while capable of producing a protease having an excellent activity and reducing mucilage-producing ability during fermentation simultaneously. Specifically, *Bacillus amyloliquefaciens* known to be used for preparing conventional fermented soy products were prepared, and strains were selected and isolated by UV irradiation for strain improvement, among them, the *Bacillus amyloliquefaciens* CJ24-34 of the present disclosure having an excellent antibacterial activity against various pathogenic microorganisms could be selected. As used herein, the term "improvement" can be achieved by means of mutation, genetic recombination, gene cloning, or the like so as to improve the defects or productivity of the strain, and the mutation may include a gene, a chromosome, or a genomic mutation. A physical mutation, a chemical mutation, or a biological mutation using UV rays may be used to induce the mutation, and UV rays can be irradiated using a UV lamp for a period of time during which a wavelength of 200 nm to 300 nm achieves a mortality rate of 95% to 100%. In the present disclosure, the UV wavelength of 254 nm is irradiated for a period of time during which the mortality rate for the wildtype strain reaches 99.99%, thereby isolating and obtaining only the mutant strains which formed colonies.

According to one embodiment, the *Bacillus amyloliquefaciens* CJ24-34 according to the present disclosure has an excellent antibacterial activity against pathogens. For example, the *Bacillus amyloliquefaciens* CJ24-34 has an antibacterial activity against at least one pathogen selected from the group consisting of *Salmonella typhimurium, Vibrio vulnificus, Vibrio parahaemolyticus, Photobacterium damsel, Listonella anguillarum,* and *Edwardsiella tarda*. The antibacterial activity can be measured using a dilution method, a disk diffusion test, E-TEST, or the like.

Specifically, *Salmonella* can cause food poisoning in livestock, and other bacteria including *Vibrio* species are known to cause diseases in farm-raised fish including sepsis, *Vibrio cholerae*, vibriosis in shrimp, pasteurellosis in yellowtail, and edwardsiellosis in flounder. With regard to these pathogenic bacteria, the *Bacillus amyloliquefaciens* according to the present disclosure effectively inhibits the growth thereof, and thus, a fermented soy product prepared by using the same or a fermented soy product containing the same may have an antibacterial activity against these pathogens.

Conventional fermented soy products have problems in that sticky mucilage is produced due to polymerization of a levan-form fructan and a polyglutamate derived from a saccharide and a protein of soy raw material, respectively, by an enzyme produced during the fermentation process. The production of such mucilage causes the fermented soy products to aggregate into lumps, which makes stirring difficult and makes it difficult to control and transfer of dissolved oxygen and temperature in the fermented products, thus causing many problems in the mass production process. The production of mucilage can be determined by measuring the viscosity or glossiness thereof by phenotypic observation of colonies or by measuring the content of a polymer substance such as poly-γ-glutamic acid.

According to one embodiment, the *Bacillus amyloliquefaciens* CJ24-34 according to the present disclosure may have a low mucilage-producing ability. More specifically, the fermented soy product produced from the *Bacillus amyloliquefaciens* has a low content of sticky mucilage and hardly aggregates into lumps, and thus, high-quality fermented soy products can be prepared using the same (see Example 4).

According to one embodiment, the *Bacillus amyloliquefaciens* CJ24-34 according to the present disclosure can produce a highly active protease and hydrolyze most of the soy protein, which is composed of polymers, decomposing it into low molecular weight peptides, thereby significantly increasing the digestion-absorption rate of the fermented soy product. The peptides of the present disclosure form a polymer by various combinations of amino acids via a peptide bond and generally consist of 2 to 50 amino acids bound together. The low molecular weight peptide is a small peptide having a low molecular weight and has the advantage of facilitating the absorption during digestion, thereby increasing its digestibility when applied as animal feed. Depending on the type and composition ratio of the low molecular weight peptide included in the desired hydrolysate to be finally prepared, the conditions of the moisture content, protein content, or the like of the soy protein concentrate, which is the raw material, can be appropriately selected and used.

According to one embodiment, the fermented soy product prepared by the *Bacillus amyloliquefaciens* according to the present disclosure may comprise 40% or more of low molecular weight peptides having a molecular weight of 30 kDa or less. More specifically, the fermented soy product comprises 40% to 100%, 50% to 95%, 60% to 90%, 70% to 90%, 75% to 90%, 75% to 85%, or 80% to 85% of peptides having a molecular weight of 30 kDa or less. In addition, the fermented soy product may comprise 15% or more of peptides having 10 kDa or less. More specifically, the fermented soy product may comprise 15% to 80%, 20% to 70%, 30% to 65%, 40% to 65%, or 50% to 60% of peptides having a molecular weight of 10 kDa or less. Said % may refer to a percentage ratio of the partial area that represents a particular molecular weight range over the total area in the protein molecular weight distribution by GPC. According to one embodiment, the fermented soy product prepared from the *Bacillus amyloliquefaciens* according to the present disclosure may have an increased protein content compared to that before fermentation. This indicates that the fermentation time can be shortened by increasing the protein content in a shorter period of time even when compared with fermented soy products fermented with a conventionally known strain. That is, the *Bacillus amyloliquefaciens* according to the present disclosure may improve the quality of a feed by significantly increasing the content of the low molecular weight peptides in the fermented soy product and may shorten the fermentation time by increasing the protein content more rapidly.

16S rRNA of the *Bacillus amyloliquefaciens* CJ24-34 strain of the present disclosure was analyzed, and as a result, it showed a close relationship with *Bacillus amyloliquefaciens* subsp. *Plantarum* FZB42T (CP000560), which is a standard strain, and the 16S rRNA gene sequence homology was confirmed to be 99.93% (1507 bp/1508 bp). Thus, the mutant strain CJ24-34 according to the present disclosure was named *Bacillus amyloliquefaciens* subsp. *Plantarum* CJ24-34 and was deposited under the Budapest Treaty at the Korean Culture of Microorganisms (KCCM) on Jun. 15, 2017, with an accession number of KCCM12038P.

According to one embodiment, the method for preparing a fermented soy product may further comprise steps of controlling the moisture content of the soybean meal or soy protein concentrate and subjecting it to heat treatment and cooling prior to inoculating the *Bacillus amyloliquefaciens* CJ24-34 strain into the soybean meal or soy protein concentrate. It is preferred to perform the heat treatment for a predetermined time after controlling the moisture content of the soybean meal or soy protein concentrate, which is a raw material, by directly spraying or mixing an appropriate amount of water before solid fermentation. Specifically, the moisture content may be controlled for the content of the proteins or low molecular weight peptides of the desired fermented soy product or for the purpose of setting fermentation time. In addition, the purpose of the heat treatment is to kill various germs in the raw material and to denature protein by destroying the cell wall of the raw material, thereby providing an environment in which the desired microorganism can grow vigorously. The heat treatment method may be performed using various methods widely known in the art without limitation. Specifically, it can be performed using steam or superheated steam.

According to one embodiment, the soybean meal or soy protein concentrate of the present disclosure may be prepared by controlling the moisture content in the range of 30% (v/w) to 80% (v/w) and performing heat treatment for 10 minutes to 30 minutes while controlling the heat treatment temperature to 70° C. to 130° C., followed by cooling to 30° C. to 50° C. The culture solution for the *Bacillus amyloliquefaciens* CJ24-34 of the present disclosure may be inoculated in an amount of 10% by weight based on the weight of each soybean meal and soybean protein concentrate and fermented at 20° C. to 50° C. for 8 hours to 72 hours.

More specifically, the controlled moisture content (v/w) of the soybean meal or soy protein concentrate may be in the range of 30% to 80%, 30% to 70%, 30% to 60%, 30% to 50%, 30% to 40%, 40% to 80%, 40% to 70%, 40% to 60%, or 40% to 50%. The moisture content of the soybean meal may be appropriately controlled to a low moisture condition or a high moisture condition for the content of the proteins or low molecular weight peptides of the desired fermented soybean meal or for the purpose of setting fermentation time.

According to one embodiment, when the heat treatment temperature is low or the treatment time is short, there is a problem in that the germicidal effect of germs may deteriorate and the subsequent fermentation process may not be smoothly carried out. In contrast, when the heat treatment temperature is high or the treatment time is long, the digestibility is decreased due to the denaturation of the proteins in the soybean meal, and thus the quality of the final product is deteriorated. Accordingly, it is preferred to select the heat treatment temperature or the treatment time within the above range in order to avoid such problems. Through the heat treatment process, it has an effect of creating a chemical environment where contaminants present in the soybean meal or soybean protein concentrate are almost killed and the subsequent solid fermentation process is smoothly carried out. Also, it is expected that the anti-nutritional factors such as trypsin inhibitor (TI) which impair the digestibility may be slightly reduced.

More specifically, the heat treatment temperature may be in the range of 70° C. to 120° C., 70° C. to 110° C., 70° C. to 100° C., 80° C. to 130° C., 80° C. to 120° C., 80° C. to 110° C., 80° C. to 100° C., 90° C. to 130° C., 90° C. to 120° C., 90° C. to 110° C., or 90° C. to 100° C. Further, the heat may be more specifically 10 minutes to 30 minutes or 20 minutes to 30 minutes.

The heat-treated soybean meal or soybean protein concentrate as described above may be cooled to a temperature at which solid fermentation is possible. The cooling process may be carried out through a transfer process using a conveyor-type air cooler. More specifically, it may be carried out until the temperature of the soybean meal or soybean protein concentrate reaches 30° C. to 50° C., 35° C. to 45° C., or 35° C. to 40° C.

The culture temperature for the fermentation may be 20° C. to 50° C., more specifically 30° C. to 50° C., 40° C. to 50° C., 30° C. to 40° C., or 20° C. to 40° C., but is not limited to and may vary depending on the quality of the desired fermented soy product. In addition, the culture time for the fermentation may be 8 hours to 72 hours, more specifically, 10 hours to 70 hours, 10 hours to 60 hours, 10 hours to 50 hours, 10 hours to 40 hours, 10 hours to 30 hours, 10 hours to 20 hours, or 8 hours to 18 hours, but is not limited thereto and may vary depending on the quality of the desired fermented soy product.

According to one embodiment, the *Bacillus amyloliquefaciens* CJ24-34 strain according to the present disclosure may be inoculated into the soybean meal or soy protein concentrate in an amount of $10^5$ CFU/g to $10^9$ CFU/g, $10^5$ CFU/g to $10^8$ CFU/g, $10^6$ CFU/g to $10^9$ CFU/g, or $10^6$ CFU/g to $10^8$ CFU/g. The amount of the strain to be inoculated may be an important factor that affects the solid fermentation of the soybean meal or soybean protein concentrate. When the amount of the strain to be inoculated is small, it may take a long time to prepare the fermented product, and thus, the fermentation time is prolonged and there is a high likelihood of contamination by other microorganisms. In contrast, when the amount of the strain to be inoculated is too high, the fermentation time may be shortened, but it may be difficult to appropriately maintain the fermentation environment. In particular, because the fermentation performance may largely depend on the growth characteristics of the fermentation strain and the type of fermentation apparatus, it is preferred to appropriately select the inoculation amount considering the characteristics of the strain in the production stage.

According to one embodiment, the fermented soy product may be obtained by inoculating the *Bacillus amyloliquefaciens* strain according to the present disclosure into the soybean meal or soybean protein concentrate, followed by solid fermentation. For example, a packed-bed fermentor may be used in the fermentation process. The packed-bed fermentor may include various types, such as a batch-type aeration culture apparatus, closed-type culture apparatus, continuous-type aeration culture apparatus, or the like, and any type can be used in the method of the present disclosure without limitation as long as it can be used for the preparation of fermented soy products, and an appropriate apparatus may be selected and used according to the production scale. For example, the soybean meal or soybean protein concentrate inoculated with the strain may be placed in the packed-bed fermenter in a thickness of 5 cm to 50 cm and fermented at 20° C. to 50° C. for 8 hours to 72 hours.

According to one embodiment, the method of the present disclosure may further comprise steps of drying and pulverizing the fermented soy product obtained after the fermentation step at low temperature and low humidity. The residual moisture content of the fermented soy product immediately after fermentation may be 20% (v/w) to 50% (v/w). A drying process may be added to prepare the final product of the fermented soy product having a moisture content of 10% (v/w) to 12% (v/w). After the fermentation has been completed, a pulverizing process may be added after the drying process so as to make the particle size of the fermented soy product uniform, as lumps may have formed in the fermented soy product. The drying and pulverization process may be carried out by various methods known in the art. However, if the drying is performed at an excessively high temperature, the live bacteria in the fermented soy product may be killed, and thus, the drying process is preferably performed at a low temperature. In addition, the pulverization process may be performed to have various sizes depending on the intended use of the fermented soy product; for example, a hammer mill may be used.

The fermented soy product prepared by using the amyloliquefaciens strain according to the present disclosure may improve the digestion-absorption rate of an animal due to a high content of the low molecular weight peptides and is thus highly applicable as a high-quality protein feed material which can substitute animal protein due to a high protein content.

According to one embodiment, the present disclosure provides a *Bacillus amyloliquefaciens* CJ24-34 strain (KCCM12038P), a culture of the strain, a concentrate of the culture, or a dried product of the culture. As described above, the strain is a novel strain, and the fermented soy product prepared using the strain has a low content of mucilage but has a high content of low molecular weight peptides and shows an antibacterial activity.

According to one embodiment, the present disclosure provides an antibacterial composition comprising a *Bacillus amyloliquefaciens* strain, a culture of the strain, a concentrate of the culture, or a dried product of the culture and having an antibacterial activity against at least one pathogen selected from the group consisting of *Salmonella typhimurium, Vibrio vulnificus, Vibrio parahaemolyticus, Photobacterium damsel, Listonella anguillarum*, and *Edwardsiella tarda*. For more details regarding the above, reference can be made to the content described above and Examples.

According to one embodiment, the present disclosure provides a feed composition comprising the fermented soy product prepared by the above method. The content of the fermented soy product in the feed composition according to the present disclosure may be properly controlled depending on the kind and age of livestock to be applied, application form, desired effects, or the like. For example, it may be used in an amount of 1% by weight to 99% by weight, more specifically 10% by weight to 90% by weight, and 20% by weight to 80% by weight, but is not limited thereto.

For administration, the feed composition of the present disclosure may further include a mixture of at least one of an organic acid such as citric acid, fumaric acid, adipic acid, lactic acid, or the like; phosphate such as potassium phosphate, sodium phosphate, polyphosphate, or the like; a natural antioxidant such as polyphenol, catechin, tocopherol, vitamin C, green tea extract, chitosan, tannic acid, or the like; in addition to the fermented soy product. If necessary, another typical additive such as an anti-influenza agent, a buffer, a bacteriostatic agent, or the like may be added. In addition, a diluent, a dispersing agent, a surfactant, a binder, or a lubricant may be additionally added to formulate the composition into an injectable preparation such as an aqueous solution, a suspension, an emulsion, or the like, a capsule, a granule, or a tablet.

Moreover, the feed composition of the present disclosure may be used together with various auxiliaries such as amino acids, inorganic salts, vitamins, antioxidants, antifungal agents, antibacterial agents, or the like, and a nutrient supplement, a growth accelerator, a digestion-absorption accelerator, and a prophylactic agent, in addition to the main ingredients including a vegetable protein feed such as pulverized or fragmented wheat, barley, corn, or the like, an animal protein feed such as blood meal, meat meal, fish meal, or the like, animal fat, and vegetable oil.

When the feed composition of the present disclosure is used as a feed additive, the feed composition may be added as it is or used together with other components, and may be appropriately used according to the typical method. The feed composition may be prepared in the administration form of an immediate-release formulation or a sustained-release formulation, in combination with non-toxic pharmaceutically acceptable carriers. The edible carriers may be corn starch, lactose, sucrose, or propylene glycol. The solid carrier may be in the administration form of tablets, powders, troches, or the like, and the liquid carrier may be in the administration form of syrups, liquid suspensions, emulsions, solutions, or the like. In addition, the administration agent may include a preservative, a lubricant, a solution accelerator, or a stabilizer and may also include other agents for improving inflammatory diseases and a substance useful for the prevention against viruses.

The feed composition of the present disclosure may be applied to an animal's diet, that is, a feed for many animals including mammals, poultry, fish, and crustaceans. It may be used in commercially important mammals such as pigs, cattle, goats, or the like, zoo animals such as elephants, camels, or the like, or livestock such as dogs, cats, etc. Commercially important poultry may include chickens, ducks, geese, or the like, and commercially grown fish and crustaceans such as trout and shrimp may also be included.

The feed composition according to the present disclosure may be mixed in an amount of approximately 10 g to 500 g, preferably 10 g to 100 g per 1 kg, based on the dry weight of the livestock feed. After being completely mixed, the feed composition may preferably be provided as mash or further subjected to a pelletizing, extensification, or extrusion process.

The *Bacillus amyloliquefaciens* CJ24-34 strain according to the present disclosure provides a use for preparing a fermented soy product.

MODE FOR THE INVENTION

The present disclosure relates to a novel *Bacillus amyloliquefaciens* CJ24-34 strain, a method for preparing a fermented soy product using the same, and a fermented product thereof. Hereinafter, the present disclosure will be described in detail by way of Examples and Experimental Examples. However, these Examples are given for illustrative purposes only, and should not be construed as limiting the scope of the present disclosure.

Hereinafter, the present disclosure will be described in detail by way of Examples and Experimental Examples.

[Example 1] Isolation of Novel *Bacillus amyloliquefaciens* Strain

*Bacillus amyloliquefaciens* (hereinafter referred to as "CJ823 strain", see Korean Patent No. 10-1517326), known to be typically used for the fermentation of a soybean meal or a soybean protein concentrate, was prepared, and then, the improvement of the strain was carried out in the following manner.

First, the CJ823 strain was activated by culturing in a TSB plate medium (medium composition: 17.0 g of enzymatic digest of casein, 3.0 g of enzymatic digest of soybean meal, 5.0 g of sodium chloride (NaCl), 2.5 g of dipotassium phosphate, 2.5 g of dextrose, 15.0 g of agar, 25° C., final pH: 7.3*0.2) at 37° C. for 12 hours. The activated strain was used as a seed culture by suspending about 2 platinum (diluted to an absorbance of about 0.2 at 660 nm) in 9 mL of a 0.8% NaCl sterilizing solution. 50 mL of the previously prepared TSB was inoculated with the seed culture suspension at 1% and then cultured at 37° C. with a speed of 180 rpm until the absorbance at 660 nm reached about 4.0 to 5.0. After culturing the seed culture, the culture solution was centrifuged (8000 rpm, 4° C., 10 minutes) to isolate the cells from the supernatant. The isolated cells were washed twice with 0.8% NaCl sterilizing solution in the same amount as the culture solution. 20 mL of the 0.8% NaCl sterilizing solution was mixed with the cells such that the cell concentration reached an absorbance at 660 nm of about 0.8, and 15 mL of the mixture was applied to a sterile petri dish. Next, UV rays were irradiated to the cells at a height of about 50 cm with a wavelength of 254 nm using a UV lamp (VIBER LOURMAT, 115 V, 60 Hz). The UV irradiation was carried out for a period of time until the mortality rate of the wildtype strain reached 99.99% according to the UV irradiation time. Subsequently, 0.1 mL of the UV-irradiated mixture was added to the TSA plate medium (medium composition: tryptic soy agar, 15 g of enzymatic digest of casein, 5 g of enzymatic digest of soybean meal, 5 g of NaCl, 15 g of agar, 25° C., final pH: 7.3±0.2) at 37° C. for 12 hours, and only the mutant strains which formed the colonies were isolated and obtained.

[Example 2] Measurement of Proteolytic Ability and Antibacterial Activity of *Bacillus amyloliquefaciens*

The proteolytic ability and antibacterial activity of each mutant strain obtained by isolation according to Example 1 were confirmed by the following method. As a control, *Bacillus subtilis* (Accession No. KCCM11438P) and *Bacillus amyloliquefaciens* (CJ823 strain) known in the art were used (hereinafter referred to as Control 1 and Control 2, respectively).

1) Proteolytic Ability

In order to measure the proteolytic ability of the mutant strains obtained in Example 1, the strains were cultured by inoculation in a YM agar medium (3.0 g of yeast extract, 3.0 g of malt extract, 10.0 g of peptone, 20.0 g of agar) containing 2% (w/v) skim milk (Difco, USA), and the size of clear zone (C) formed by degradation of the substrate was measured at the same time while measuring the diameter of the colony formed (growth (G)).

More specifically, each mutant strain was cultured in the TSB medium (medium composition: 17.0 g of enzymatic digest of casein, 3.0 g of enzymatic digest of soybean meal, 5.0 g of NaCl, 2.5 g of dipotassium phosphate, 2.5 g of dextrose, final pH: 7.3±0.2 at 25° C.) at 37° C. for 12 hours with a stirring speed of 200 rpm. Then, 1.0 µL of the culture solution for each mutant strain was aliquoted to the YM agar medium containing skim milk and cultured at 37° C. for 16 hours. After the completion of the culture, the diameter (G) of the colonies formed on the culture medium and the size (C) of the clear zone were measured.

2) Antibacterial Activity Against *Salmonella typhimurium*

*Salmonella typhimurium* (ATCC14028), a typical pathogen capable of causing disease in livestock, was used in order to measure the antibacterial activity of the mutant strains obtained in Example 1 above. More specifically, the mutant strains were each cultured in a GYP medium (medium composition: 10 g of glucose, 8 g of yeast extract, 2 g of polypeptone, pH: 7.0) at 37° C. for 12 hours at a stirring speed of 180 rpm. 1.5 µL of the culture solution for each mutant strain was aliquoted to a GYP agar medium (medium composition: 10 g of glucose, 8 g of yeast extract, 2 g of polypeptone, 15 g of agar, pH: 7.0) supplemented with $1 \times 10^5$ CFU/mL of *Salmonella typhimurium* and cultured for 37° C. for 15 hours. After the completion of the culture, the size of clear zone formed around the colonies of the mutant strains was measured and the titer of the antibacterial activity was measured.

TABLE 1

| Name of strain | C | G | C/G | C − G | Antibacterial activity |
|---|---|---|---|---|---|
| Control 1 | 6.6 | 6.6 | 1.00 | 0.00 | ++ |
| Control 2 | 12.46 | 8.31 | 1.50 | 4.15 | ++++ |
| CJ24-1 | 13.02 | 7.05 | 1.85 | 5.97 | +++++ |
| CJ24-3 | 13.91 | 6.78 | 2.05 | 7.13 | +++++ |
| CJ24-4 | 14 | 6.76 | 2.07 | 7.24 | +++++ |
| CJ24-5 | 14.06 | 7.02 | 2.00 | 7.04 | +++++ |
| CJ24-6 | 13.79 | 6.78 | 2.03 | 7.01 | +++++ |
| CJ24-7 | 13.56 | 6.57 | 2.06 | 6.99 | +++++ |
| CJ24-9 | 13.45 | 6.34 | 2.12 | 7.11 | +++++ |
| CJ24-10 | 13.15 | 6.46 | 2.04 | 6.69 | +++++ |
| CJ24-11 | 13.5 | 6.82 | 1.98 | 6.68 | +++++ |
| CJ24-12 | 13.31 | 6.68 | 1.99 | 6.63 | +++++ |
| CJ24-13 | 13.76 | 6.62 | 2.08 | 7.14 | +++++ |
| CJ24-14 | 13.6 | 7.23 | 1.88 | 6.37 | − |
| CJ24-15 | 14.15 | 6.94 | 2.04 | 7.21 | +++++ |
| CJ24-16 | 13.26 | 5.92 | 2.24 | 7.34 | +++++ |
| CJ24-17 | 13.27 | 6.07 | 2.19 | 7.20 | +++++ |
| CJ24-18 | 13.37 | 5.95 | 2.25 | 7.42 | +++++ |
| CJ24-19 | 13.7 | 6.94 | 1.97 | 6.76 | +++++ |
| CJ24-20 | 13.94 | 7.38 | 1.89 | 6.56 | +++++ |
| CJ24-21 | 13.18 | 6.86 | 1.92 | 6.32 | +++++ |
| CJ24-22 | 13.26 | 6.35 | 2.09 | 6.91 | ++++ |
| CJ24-23 | 13.73 | 6.69 | 2.05 | 7.04 | +++++ |
| CJ24-24 | 13.79 | 7.5 | 1.84 | 6.29 | +++++ |
| CJ24-25 | 13.4 | 6.45 | 2.08 | 6.95 | +++++ |
| CJ24-26 | 14.08 | 7.23 | 1.95 | 6.85 | +++++ |
| CJ24-27 | 13.9 | 7.93 | 1.75 | 5.97 | ++ |
| CJ24-28 | 13.82 | 5.92 | 2.33 | 7.90 | +++++ |
| CJ24-29 | 13.93 | 5.87 | 2.37 | 8.06 | +++++ |
| CJ24-30 | 13.55 | 5.99 | 2.26 | 7.56 | +++++ |
| CJ24-31 | 13.22 | 5.91 | 2.24 | 7.31 | ++++ |
| CJ24-32 | 13.64 | 5.81 | 2.35 | 7.83 | +++ |
| CJ24-33 | 13.91 | 6.11 | 2.28 | 7.80 | ++++ |
| CJ24-34 | 14.13 | 6.21 | 2.28 | 7.92 | +++++ |
| CJ24-35 | 15.11 | 7.13 | 2.12 | 7.98 | + |
| CJ24-36 | 12.91 | 5.11 | 2.53 | 7.80 | +++ |

Table 1 shows the antibacterial activity through the measurements of the size of the clear zone (C), the diameter of the colony (G), the ratio thereof (C/G), the size difference thereof (C-G), and the size of clear zone measured after the culture of the strains was completed.

According to Table 1, among the mutant strains, CJ24-28, CJ24-29, CJ24-32, CJ24-33, CJ24-34, and CJ24-36 had a higher ratio of the size of the clear zone to the size of the colonies formed (C/G) (2.28-2.53), among which CJ24-28, CJ24-29, and CJ24-34 had the highest antibacterial activity (all +++++). In contrast, Control 1 had the lowest C/G value, and Control 2 had the second lowest C/G value (1.00 and 1.50, respectively), and the antibacterial activities thereof were only ++ and ++++, respectively. That is, it was confirmed that the mutant strains had enhanced proteolytic ability and antibacterial activity compared to the conventionally known *Bacillus subtilis* and *Bacillus amyloliquefaciens*. Thus, when the strains were applied to a soybean protein concentrate or a soybean meal to prepare a fermented soy product, it could be expected that the fermented soy product would show an antibacterial activity.

[Example 3] Measurement of Antibacterial Activity of CJ24-34 Strain

An experiment was further conducted to confirm whether the CJ24-34 strain, which had an excellent proteolytic ability because of the largest size of the clear zone (C) and the diameter of the colony (G) among the strains (CJ24-28, CJ24-29, and CJ24-34) selected as having an excellent antibacterial activity in Example 2, has an antibacterial activity of against pathogenic microorganisms other than *Salmonella*. In order to confirm the antibacterial activity, pathogenic microorganisms such as *Vibrio vulnificus, Vibrio parahaemolyticus, Photobacterium damsel, Listonella anguillarum, Lactococcus garvieae*, and *Edwardsiella tarda* were used, and they are known to cause disease in farm-raised fish such as sepsis, *Vibrio cholerae*, vibriosis in shrimp, pasteurellosis in yellowtail, streptococcosis in flounder, and edwardsiellosis in flounder. Among the pathogenic microorganisms, *Vibrio vulnificus, Vibrio parahaemolyticus, Photobacterium damsel*, and *Lactococcus garvieae* were strains obtained from Gyeongsang National University Hospital Branch of National Culture Collection to Pathogens, and *Listonella anguillarum* and *Edwardsiella tarda* were strains obtained from KCTC. Each pathogenic microorganism was cultured in the corresponding medium and temperature according to Table 2 below. Then, single colonies were selected, and they were transferred to a test tube and pre-cultured in the corresponding liquid medium overnight. The pre-culture solution was again inoculated at 0.1% into 100 mL of the corresponding liquid medium for each pathogenic bacterium and cultured for about 12 hours. The culture solution was used for preparing an agar medium for each pathogenic bacterium for testing antibacterial activity.

TABLE 2

| Pathogenic bacteria | Induced disease | Accession No. | Culture condition | | |
|---|---|---|---|---|---|
| | | | Agar medium | Liquid medium | Temperature (° C.) |
| *Vibrio vulnificus* | Vibriosis in shrimp | P4710 | Marine agar (BD Difco) | Marine broth (BD Difco) | 30 |
| *Vibrio parahaemolyticus* | Vibriosis in shrimp | P4712 | Marine agar (BD Difco) | Marine broth (BD Difco) | 30 |
| *Photobacterium damsela* | Pasteurellosis in yellowtail | P4482 | Marine agar (BD Difco) | Marine broth (BD Difco) | 30 |
| *Listonella anguillarum* | Vibriosis in yellowtail | KCTC 2711 | MRS agar (BD Difco) | MRS broth (BD Difco) | 30 |
| *Lactococcus garvieae* | Streptococcosis in flounder | P4737 | Marine agar (BD Difco) | Marine broth (BD Difco) | 30 |
| *Edwardsiella tarda* | Edwardsiellosis in flounder | KCTC 12267 | Nutrient broth (BD Difco) + 0.2% agar | Nutrient broth (BD Difco) | 37 |

The single colonies obtained by culturing CJ24-34 of this application in the GYP agar medium (1% glucose, 0.8% yeast extract, 0.2% peptone, 0.2% agar) were inoculated into a test tube containing 3 mL of a GYP medium (1% glucose, 0.8% yeast extract, 0.2% peptone) and pre-cultured at 37° C. with a speed of 180 rpm overnight. The pre-culture solution was again inoculated at 0.1% into 100 mL of the GYP medium and cultured at 37° C. with a speed of 180 rpm. Next, the culture solutions after 16 hours and 20 hours of the culture were secured, and 10 mL of each culture solution was centrifuged with a speed of 8000 rpm for 10 minutes at 4° C. to recover the supernatant. The supernatant was again filtered through a 0.2 µm syringe filter to prepare a filtrate.

In order to test the antibacterial activity of the antibacterial substances secreted from the CJ24-34 strain in the agar medium, an agar medium corresponding to the culture conditions of each pathogenic bacterium was prepared and sterilized at 121° C. for 15 minutes. The agar medium was cooled, and the culture solution of each pathogenic bacterium prepared in advance before the agar medium was solidified was added to the agar medium at 1% and mixed, and then the mixture was transferred to a square plate to solidify the agar media inoculated with each pathogenic bacterium. A peni cylinder cup was placed on the fully solidified agar medium plate, and 300 µL of each CJ24-34 filtrate (16 hours, 20 hours) prepared in advance was loaded in each cup, and the corresponding bacteria were cultured according to the culture conditions of each pathogenic bacterium. After the completion of the culture, the size of the clear zone appeared in the agar medium cultured with each pathogenic bacterium was measured. At this time, the size of the peni cylinder cup was 7 mm, and the size of the clear zone was compared by measuring the diameter of the spot including the clear zone generated by the antibacterial substance. An increase in the size of the clear zone indicates that the pathogenic bacteria could not grow due to the antibacterial substances secreted by CJ24-34. In addition, in this experiment, the clear zone generated inside of the peni cylinder cup was interpreted as an indicator of the antibacterial activity, but the size thereof was not measured as the clear zone generated outside of the peni cylinder cup.

TABLE 3

| Pathogenic bacteria | Induced disease | Accession No. | Size of clear zone according to culture time (mm) * size of peni cylinder cup: 7 mm | |
|---|---|---|---|---|
| | | | 16 hours | 20 hours |
| *Vibrio vulnificus* | Vibriosis in shrimp | P4710 | 9 | 10 |
| *Vibrio parahaemolyticus* | Vibriosis in shrimp | P4712 | 7 (inner clear zone generated) | 7 (inner clear zone generated) |
| *Photobacterium damsela* | Pasteurellosis in yellowtail | P4482 | 15 | 15 |
| *Listonella anguillarum* | Vibriosis in yellowtail | KCTC 2711 | 14 | 14 |
| *Lactococcus garviaeae* | Streptococcosis in flounder | P4737 | No clear zone | No clear zone |
| *Edwardsiella tarda* | Edwardsiellosis in flounder | KCTC 12267 | 25 | 25 |

With reference to the size of the clear zone described in Table 3, it was confirmed that the CJ24-34 of the present disclosure secreted antibacterial substances having an antibacterial activity against a specific pathogenic bacterium. The size of the peni cylinder cup was 7 mm, and based on this, it was confirmed that the antibacterial substances of CJ24-34 inhibited the growth of *Vibrio vulnificus, Photobacterium damsel, Listonella anguillarum*, and *Edwardsiella tarda*. Meanwhile, the size of clear zone of *Vibrio parahaemolyticus* was 7 mm, which was the same as the size of the peni cylinder cup, and it could be evaluated as having no antibacterial activity when measuring the size of the external clear zone. However, it was confirmed that the clear zone existed partially inside of the peni cylinder cup when substantially viewed on the plate, and thus, it can be inferred that there was some antibacterial activity against this pathogen. That is, the CJ24-34 strain showed an antibacterial activity against 5 pathogenic bacteria (*Vibrio vulnificus, Vibrio parahaemolyticus, Photobacterium damsel, Listonella anguillarum*, and *Edwardsiella tarda*) among 6 pathogenic bacteria tested in this experiment. Thus, when the CJ24-34 strain of the present disclosure is applied to a soy protein concentrate or a soybean meal, it is expected that a fermented soy product, in which the proliferation of pathogenic bacteria is prevented, and an animal feed composition containing the same can be prepared.

[Example 4] Measurement of Mucilage-Producing Ability of *Bacillus amyloliquefaciens*

In order to confirm the mucilage-producing ability of the mutant strains CJ24-28, CJ24-29, and CJ24-34, which were selected as having excellent proteolytic ability and antibacterial activity in Example 2, the strains were further cultured in the GYP agar medium, and the phenotype of each colony was closely observed. As a control group, Control 2 (*Bacillus amyloliquefaciens*, CJ823 strain) described in Example 2 was used.

As a result of the experiment, the strain colony of Control 2 was observed to be viscous and glossy, which confirmed the mucilage production, whereas in the colonies of the mutant strains CJ24-28, CJ24-29, and CJ24-34 selected in Example 2, it was confirmed that mucilage production was suppressed as no glossiness or viscosity was observed.

[Example 5] Mucilage-Producing Ability and Fermentation Ability of CJ24-34 Strain in Soy Protein Concentrate An experiment was conducted to confirm the mucilage production and fermentation ability of the strains when the CJ24-34 strain, which was confirmed to have excellent proteolytic ability and antibacterial activity among the mutant strains selected in Example 2 and Example 3, was fermented by being inoculated into the soybean protein concentrate. As a control group thereof, Control group 1 (*Bacillus subtilis*: Accession No. KCCM11438P) and Control 2 (*Bacillus amyloliquefaciens*: CJ823) mentioned in Example 2 were both used.

The CJ24-34 strain was pre-cultured in the GYP medium (medium composition: glucose 10 g/L, yeast extract 8 g/L, soy peptone 2 g/L), and the culture solution obtained by the pre-culture was inoculated again into the GYP medium such that the amount thereof accounted for 1% and cultured until the absorbance at 660 nm was 6 or more.

The soy protein concentrate was prepared by controlling the moisture content to about 43% (v/w) and heat treating at 100° C. for 30 minutes, followed by cooling to 30° C. to 50° C. 10% by weight of the culture solution of the CJ24-34 strain was inoculated into the pre-treated soy protein concentrate based on the weight of the soy protein concentrate, and the moisture content of the inoculated culture solution was controlled to about 46%.

The soy protein concentrate was fermented for 16 hours in a constant temperature and humidity chamber maintained at a temperature of 37° C. and a humidity of 95%. Before fermentation, the pH of the soy protein concentrate was about 6.8, and each strain was inoculated in an amount of about $10^7$ CFU/g. After the completion of the fermentation, the production of mucilage was examined, and the moisture, viable cell count, and pH of the fermented product were again measured.

The protein content and increase in protein content of the fermented product were measured based on the dry weight after drying the fermented product.

FIG. 1 is a photograph showing fermented soy protein concentrates fermented by applying CJ24-34 and two control strains. FIGS. 1A and C are photographs of fermented soy protein concentrates fermented with Control 1 (*Bacillus subtilis*) and CJ24-34 according to the present disclosure, respectively, and it was confirmed that the mucilage production was suppressed as no viscosity or lumps were observed in the fermented products. In contrast, FIG. 1B is a photograph of the fermented soybean protein concentrate fermented with Control 2 (*Bacillus amyloliquefaciens*). The fermented product was very viscous and formed lumps. That is, the conventional *Bacillus amyloliquefaciens* produces a considerable amount of mucilage during the fermentation process, whereas the *Bacillus amyloliquefaciens* CJ24-34 according to the present disclosure hardly produces mucilage, thereby confirming that it can be useful for mass production of the fermented product.

1) SDS-PAGE (Polyacrylamide Gel Electrophoresis)

100 mg of the raw material (soy protein concentrate) and the fermented soy protein concentrates (the fermented soy protein concentrate of CJ24-34 and the fermented soy protein concentrate of Control 1) prepared according to Example 5 were each suspended in 5 mL of 8 M urea solvent, sonicated, and then centrifuged (at 8000 rpm for 10 minutes) to isolate the supernatant. The supernatant was quantified as bicinchoninic acid and loaded onto SDS-PAGE gel.

FIG. 2 is a diagram showing SDS-PAGE results of the fermented soy protein concentrates. From the left lane of FIG. 2, M represents biomarker, 1 represents the protein distribution of the raw material (soy protein concentrate), 2 and 3 represent the protein distribution of the fermented soy protein concentrate of CJ24-34 according to the present disclosure, and 4 and 5 represent the protein distribution of the fermented soy protein concentrate of Control 1. According to the protein distribution shown in FIG. 2, it could be confirmed that the fermented soy protein concentrate of CJ24-34 according to the present disclosure contained almost no polymer protein and was mostly composed of low molecular weight peptides, and thus, an improvement in the digestion-absorption rate could be expected when the cor-

TABLE 4

| Name of strain | Time (hours) | Moisture (%) | Viable cell count (CFU/g) | pH | Protein content(%, dry weight) | Increase in protein content(%, dry weight) |
|---|---|---|---|---|---|---|
| Control 1 | 0 | 45.49 | $1.1 \times 10^8$ | 6.84 | 63.3 | |
| (*Bacillus subtilis*) | 16 | 38.94 | $7.8 \times 10^9$ | 8.45 | 68.0 | 4.0 |
| Control 2 | 0 | 45.94 | $1.6 \times 10^8$ | 6.76 | 63.9 | |
| (CJ823) | 16 | 39.19 | $4.6 \times 10^9$ | 8.23 | 68.0 | 4.1 |
| CJ24-34 of | 0 | 45.86 | $6.1 \times 10^7$ | 6.83 | 64.2 | |
| the present disclosure | 16 | 37.73 | $1.8 \times 10^9$ | 8.28 | 68.3 | 4.0 |

In order to examine the characteristics of the fermented product prepared using CJ24-34 of the present disclosure, the moisture content according to time (0 hours, 16 hours), viable cell count, pH, protein content, and increase in protein content of the fermented soy protein concentrates, in which each strain including the controls was applied, were confirmed (Table 4). As a result of the experiment, the fermented soy protein concentrate fermented with CJ24-34 according to the present disclosure had a moisture content of about 37% to 39%, a pH of 8 or more, and a viable cell count of about $10^9$ CFU/g or more. In addition, the protein content was increased by about 4% relative to the protein content of the raw material, confirming fermentation ability.

[Example 6] Protein Degradation and Molecular Weight Distribution of Fermented Soy Protein Concentrate In this Example, the protein degradation and molecular weight distribution of the fermented soy protein concentrates of Example 5 were analyzed so as to confirm the size and distribution of the peptides included in the fermented product. They were measured by SDS-PAGE and GPC, respectively.

responding strain was applied as a feed. In contrast, the fermented soy protein concentrate of Control 1 still contained the polymer proteins, confirming that the polymer proteins were not decomposed properly.

2) GPC (Gel Permeation Chromatography)

The GPC is a method to derive the protein molecular weight distribution in a sample to be measured, by analyzing standard proteins having different molecular weights to determine the retention time of each protein, and then by calculating a standard curve for the relationship between the molecular weight and the retention time. More specifically, after the retention time of the protein having a specific molecular weight is calculated, the chromatogram is divided into parts according to the time, and the ratio of partial area of each molecular weight range in the entire chromatogram area is calculated.

100 mg of the raw material (soy protein concentrate) and the fermented soy protein concentrates (the fermented soy protein concentrate of CJ24-34 and the fermented soy protein concentrate of Control 1) prepared according to Example 5 were each suspended in 5 mL of 8 M urea solvent, sonicated, and then centrifuged (at 8000 rpm for 10 minutes) to isolate the supernatant. Subsequently, the supernatant was filtered through a 0.45 µm syringe filter, and the filtrate was analyzed by GPC. The results are shown in Table 5.

TABLE 5

| MW (kDa) | Raw material (soy protein concentrate) | Fermented soy protein concentrate of CJ24-34 (1) | Fermented soy protein concentrate of CJ24-34 (2) | Fermented soy protein concentrate of Control 1 (1) | Fermented soy protein concentrate of Control 1 (2) |
|---|---|---|---|---|---|
| >75 | 22.40 | 5.59 | 6.05 | 17.22 | 18.28 |
| 30-75 | 46.99 | 14.07 | 13.57 | 36.30 | 38.08 |
| 10-30 | 15.92 | 24.57 | 24.27 | 21.99 | 20.71 |
| 5-10 | 4.70 | 22.04 | 21.86 | 8.94 | 8.17 |
| <5 | 9.98 | 33.73 | 34.26 | 15.54 | 14.76 |
| Total | 100.00 | 100.00 | 100.00 | 100.00 | 100.00 |

Table 5 shows GPC results of the raw material and the fermented soy protein concentrates. As shown in Table 5, the fermented soy protein concentrates (1) and (2) of CJ24-34 according to the present disclosure contained about 80% of peptides having a molecular weight of 30 kDa or less and about 55% of peptides having a molecular weight of 10 kDa or less, confirming that they were largely composed of low molecular weight peptides. In contrast, although the fermented soy protein concentrates of Control 1 contained more of low molecular weight peptides compared to the raw material, the content of the peptides having a molecular weight of 10 kDa or less was only about 23% to 24%, confirming that they were mostly composed of high molecular weight peptides.

[Example 7] Soybean Meal Fermentation Ability, Protein Degradation, and Molecular Weight Distribution of CJ24-34 Strain In order to confirm whether the Bacillus amyloliquefaciens CJ24-34 strain according to the present disclosure has an excellent fermentation ability even when applied to a soybean meal, two kinds of Bacillus amyloliquefaciens (KCCM11471P and KCCM11906P), which were conventionally used as a production strain of fermented soybean meals, were used as a control, and their fermentation ability was confirmed. KCCM11471P and KCCM11906P were labeled as Control 3 and Control group 4, respectively.

The Bacillus strains were pre-cultured in the GYP medium (medium composition: glucose 10 g/L, yeast extract 8 g/L, soy peptone 2 g/L), and the culture solution obtained by the pre-culture was inoculated again into the GYP medium at 1% and cultured until the absorbance at 660 nm reached 6 or more.

The soybean meal was prepared by controlling the moisture content to about 43% (v/w) and heat treating at 100° C. for 30 minutes, followed by cooling to 30° C. to 50° C. 10% by weight of the Bacillus culture solutions were each inoculated into the pre-treated soybean meal based on the weight of the soybean meal, and the moisture content of the inoculated culture solution was controlled to about 46%. Before fermentation, the pH of the soybean meal was about 6.8, and each strain was inoculated in an amount of about $10^7$ CFU/g. The soybean meal inoculated with the culture solution was fermented for 18 hours in a constant temperature and humidity chamber maintained at a temperature of 37° C. and a humidity of 95%. The fermented soybean meal after 14, 16, and 18 hours from the start of fermentation was sampled and the change in the protein content over time was measured, and the results are shown in Table 6.

TABLE 6

| Category | Fermentation time (hours) | Fermented soybean meal of Control 3 | Fermented soybean meal of Control 4 | | Fermented soybean meal of CJ24-34 | | |
|---|---|---|---|---|---|---|---|
| | | 1 | 1 | 2 | 1 | 2 | 3 |
| Protein content (%, dry weight) | 0 | 54.1 | 54.2 | 54.1 | 54.2 | 54.1 | 54.1 |
| | 14 | 58.9 | 59.5 | 59.6 | 59.9 | 59.9 | 60.0 |
| | 16 | 59.4 | 59.7 | 59.5 | 60.2 | 60.0 | 60.0 |
| | 18 | 59.4 | 59.6 | 59.8 | 60.8 | 60.5 | 60.1 |
| Increase in protein content (%, dry weight) | 14 | 4.7 | 5.3 | 5.5 | 5.7 | 5.8 | 5.9 |
| | 16 | 5.3 | 5.5 | 5.4 | 6 | 5.9 | 5.9 |
| | 18 | 5.2 | 5.4 | 5.6 | 6.6 | 6.3 | 5.9 |

Table 6 shows the protein content and the increase in protein content of the fermented soybean meals. As shown in Table 6, the protein content and the increase in protein content of the fermented soybean meal of CJ24-34 were higher than those of Control 3 or Control 4. More specifically, when the fermentation was carried out for the same amount of time, the protein content of CJ24-34 fermented soybean meal was about 1% higher than that of Control 3 and about 0.5% higher than that of Control 4 on average. From the viewpoint of technique for preparing a fermented soybean meal, it is very important to shorten the fermentation time by rapidly increasing the protein content, and thus, the *Bacillus amyloliquefaciens* CJ24-34 of the present disclosure has advantages in that it can improve the productivity of the fermented soy product and reduce the production cost.

Meanwhile, in order to confirm the size of the peptides constituting the fermented soybean meal, the protein degradation and molecular weight distribution of the fermented soybean meal fermented with CJ24-34 and the raw material (soybean meal) were analyzed. In this regard, GPC was used in the same manner as described in Example 6.

FIG. 3 is a diagram showing SDS-PAGE results of the raw material (soybean meal) and the fermented soybean meal fermented with CJ24-34. From the left lane of FIG. 3, M represents biomarker, 1 represents the protein distribution of the raw material (soybean meal), and 2 represents the protein distribution of the fermented soybean meal fermented with CJ24-34 according to the present disclosure. As shown in FIG. 3, it was confirmed that the fermented soybean meal of CJ24-34 according to the present disclosure contained almost no polymer protein and was mostly composed of low molecular weight peptides, and thus, an improvement in the digestion-absorption rate could be expected when the corresponding strain was applied as a feed.

TABLE 7

| MW (kDa) | Raw material (soybean meal) | Fermented soybean meal of CJ24-34 |
|---|---|---|
| >75 | 44.9% | 8.1% |
| 30-75 | 36.9% | 10.0% |
| 10-30 | 9.1% | 23.5% |
| 5-10 | 2.4% | 22.5% |
| <5 | 6.7% | 35.9% |
| Total | 100.0% | 100.0% |

Table 7 shows GPC results for examining the peptide composition of the raw material (soybean meal) and the fermented soybean meal. As shown in Table 7, the raw material (soybean meal) contained about 82% of peptides having a molecular weight of 30 kDa or more and was mostly composed of high molecular weight peptides. In contrast, the fermented soybean meal fermented with CJ24-34 according to the present disclosure contained about 82% of peptides having a molecular weight of 30 kDa or less and about 58% of peptides having a molecular weight of 10 kDa or less, confirming that it was largely composed of low molecular weight peptides. That is, most of the polymer proteins contained in the raw material were decomposed into low molecular weight peptides, and thus, it can be expected that the digestibility may increase when the strain is applied as a feed.

[Example 8] Soybean Meal Fermentation Ability of CJ24-34 Under Low Moisture Condition The CJ24-34 strain according to the present disclosure was pre-cultured in the GYP medium (medium composition: glucose 10 g/L, yeast extract 8 g/L, soy peptone 2 g/L), and the culture solution obtained by the pre-culture was inoculated again into the GYP medium at 1% and cultured until the absorbance at 660 nm reached 6 or more.

The soybean meal was prepared by controlling the moisture content to about 31% (v/w) and heat treating at 100° C. for 30 minutes, followed by cooling to 30° C. to 50° C. 10% by weight of the *Bacillus* culture solution was inoculated into the pre-treated soybean meal based on the weight of the soybean meal, and the moisture content of the inoculated culture medium was controlled under a low moisture condition of about 36%. The soybean meal inoculated with the culture solution was fermented for 12 hours in a constant temperature and humidity chamber maintained at a temperature of 37° C. and a humidity of 95%. The fermented soybean meal at 8, 10, and 12 hours from the start of fermentation was sampled, and the moisture content, viable cell count, protein content, and increase in protein content were measured.

TABLE 8

| Time (hours) | Moisture (%) | Viable cell count (CFU/g) | Protein content(%, dry weight) | Increase in protein content(%, dry weight) |
|---|---|---|---|---|
| 0 | 37.1 | $4.4 \times 10^8$ | 52.34 | |
| 8 | 35.15 | $8.2 \times 10^9$ | 54.6 | 2.26 |
| 10 | 33.25 | $7.6 \times 10^9$ | 55.93 | 3.59 |
| 12 | 31.55 | $7.0 \times 10^9$ | 56.1 | 3.76 |

As shown in Table 8, as the fermentation time passed, the moisture content gradually decreased and the viable cell count increased to $7.0 \times 10^9$ CFU/g. In addition, as the sugar content of the soybean meal was utilized during the growth of *Bacillus*, it was confirmed that the protein content was increased by about 4% after 12 hours in the fermented product. That is, it was confirmed that the strain according to the present disclosure had a fermentation ability even in the soybean meal under a low moisture condition. In order to confirm the composition of the size of peptides in the soybean meal under a low moisture condition, SDS-PAGE and GPC were analyzed in the same manner as described in Example 6 so as to confirm the protein degradation and molecular weight distribution.

FIG. 4 is a diagram showing SDS-PAGE results of the fermented soybean meal under a low moisture condition. From the left lane of FIG. 4, M represents biomarker, 1 represents the protein distribution of the raw material (soybean meal), and 2, 3, and 4 represent the protein distribution of the fermented soybean meal fermented for 8 hours, 10 hours, and 12 hours, respectively. As shown in FIG. 4, as the polymer proteins of the soybean meal raw material were decomposed during the fermentation, the content of low molecular weight peptides increased, thereby confirming that this could bring about an effect of increasing digestibility when applied to a feed.

TABLE 9

| Molecular weight (kDa) | Raw material (Soybean meal) | Fermented soybean meal after 8 hours | Fermented soybean meal after 10 hours | Fermented soybean meal after 12 hours |
|---|---|---|---|---|
| >75 | 54.9 | 27.5 | 21.6 | 20.9 |
| 30-75 | 28.8 | 30.2 | 27.1 | 27.1 |
| 10-30 | 8.0 | 22.9 | 26.7 | 27.2 |
| 5-10 | 2.2 | 9.1 | 12.2 | 12.4 |
| <5 | 6.1 | 10.3 | 12.5 | 12.4 |
| Total | 100.0 | 100.0 | 100.0 | 100.0 |

Table 9 shows GPC results of the fermented soybean meal under a low moisture condition according to the raw material and fermentation time (8, 10, 12 hours). As shown in Table 9, the fermented soy product fermented with the CJ24-34 strain according to the present disclosure for 12 hours contained about 52% of peptides having a molecular weight of 30 kDa or less and about 24.8% of peptides having a molecular weight of 10 kDa or less. In contrast, the raw material (soybean meal) was mostly composed of polymer peptides, which contained about 16.3% of peptides having a molecular weight of 30 kDa or less. That is, it could be confirmed that a considerable amount of the polymer proteins contained in the raw material was decomposed into low molecular weight peptides, and thus, it could be expected that the soybean meal fermented with the CJ24-34 strain of the present disclosure may bring about an increase in digestion when applied to a feed due to a high content of the low molecular weight peptides.

[Example 9] 16S rRNA Gene Sequence and Phylogenetic Analysis of Mutant *Bacillus amyloliquefaciens* CJ24-34 Strain of the Present Disclosure For the identification of the CJ24-34 mutant strain of the present disclosure, the 16S rRNA gene sequence of the strain was analyzed using the sequences shown in Table 10 below.

For the identification of the strain by the sequences of the 16S rRNA gene, the strain was amplified by PCR using 27F (5'-AGA GTT TGA TCC TGG CTC AG-3', SEQ ID NO. 1) and 1492R (5'-GGT TAC CTT GTT ACG ACT T-3', SEQ ID NO. 2) as a universal primer, and then purified. For the determination of the sequences, 27F (5'-AGA GTT TGA TCC TGG CTC AG-3', SEQ ID NO. 1), 518F (5'-CCA GCA GCC GCG GTA ATA CG-3', SEQ ID NO. 3), 805R (5'-TAC CAG GGT ATC TAA TCC-3', SEQ ID NO. 4), and 1492R (5'-GGT TAC CTT GTT ACG ACT T-3', SEQ ID NO. 2) were used to analyze the sequences of 1508 bp. The sequences were sequenced using BigDye® Terminator v3.1 Cycle Sequencing Kits (Applied Biosystems Inc., USA) and analyzed by ABI 3730XL DNA Analyzer (Applied Biosystems, 3.850 Lincoln Centre Drive, Foster City, Calif. 94404, USA).

TABLE 10

| | |
|---|---|
| SEQ ID NO. 1 | 5'-AGA GTT TGA TCC TGG CTC AG-3' |
| SEQ ID NO. 2 | 5'-GGT TAC CTT GTT ACG ACT T-3' |
| SEQ ID NO. 3 | 5'-CCAGCAGCCGCGGTAATACG-3' |
| SEQ ID NO. 4 | 5'-TACCAGGGTATCTAATCC-3' |
| SEQ ID NO. 5 | 16S rRNA sequence of *Bacillus amyloliquefaciens* subsp. *plantarum* CJ24-34 |

As the result of analyzing the sequences of 16S rRNA, it was confirmed that the CJ24-34 mutant strain of the present disclosure contained the 16S rRNA sequences of SEQ ID NO. 5. The sequence listing is enclosed at the end of the Drawings. The similarity of gene sequences was determined by comparison with the sequences registered from the EzTaxon server (http://eztaxon-e.ezbiocloud.net/) and GenBank/EMBL/DDBJ.

After performing a multiple sequence alignment using the sequences, a phylogenic tree was created using the MEGA 6 program and the taxonomic position was analyzed (FIG. 5).

As a result of the phylogenetic analysis, the CJ24-34 mutant strain of the present disclosure showed a close relationship with *Bacillus amyloliquefaciens* subsp. *Plantarum* FZB42T (CP000560), which is a standard strain, and the 16S rRNA gene sequence homology was confirmed to be 99.93% (1507 bp/1508 bp).

The mutant strain CJ24-34 according to the present disclosure was named *Bacillus amyloliquefaciens* subsp. *Plantarum* CJ24-34 and was deposited under the Budapest Treaty at the Korean Culture of Microorganisms (KCCM) on Jun. 15, 2017, with an

The invention claimed is:

1. A method for preparing a fermented soy product comprising:
   inoculating a *Bacillus amyloliquefaciens* CJ24-34 (KCCM12038P) strain into a soybean meal or a soy protein concentrate; and
   culturing the *Bacillus amyloliquefaciens* strain, thereby obtaining a fermented soy product.

2. The method for preparing a fermented soy product of claim 1, wherein the fermented soy product has an antibacterial activity against at least one pathogen selected from the group consisting of *Salmonella typhimurium*, *Vibrio vulnificus*, *Vibrio parahaemolyticus*, *Photobacterium damsel*, *Listonella anguillarum*, and *Edwardsiella tarda*.

3. The method for preparing a fermented soy product of claim 1, wherein the fermented soy product comprises 40% or more of low molecular weight peptides having a molecular weight of 30 kDa or less.

4. The method for preparing a fermented soy product according to claim 1, further comprising controlling the moisture content of the soybean meal or soy protein concentrate and heat treating the soybean meal or soy protein concentrate prior to inoculating the strain into the soybean meal or soy protein concentrate.

5. The method for preparing a fermented soy product of claim 4, wherein the moisture content of the soybean meal or fermented soy protein concentrate is controlled in the range of 30% (v/w) to 80% (v/w), and the heat treatment is performed at 70° C. to 130° C. for 10 minutes to 30 minutes.

6. The method for preparing a fermented soy product according to claim 1, wherein the *Bacillus amyloliquefaciens* CJ24-34 (KCCM12038P) strain is inoculated at a cell count of $10^5$ CFU/g to $10^9$ CFU/g.

7. The method for preparing a fermented soy product according to claim 1, wherein the culture is performed at 20° C. to 50° C. for 8 hours to 72 hours.

8. The method for preparing a fermented soy product according to claim 1, further comprising drying and pulverizing the fermented soybean meal or fermented soy protein concentrate.

9. The method for preparing a fermented soy product of claim 1, wherein the fermented soy product is a fermented soybean meal.

10. The method for preparing a fermented soy product of claim 1, wherein the fermented soy product is a fermented soy protein concentrate.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: universal primer for 16S rRNA for
      identification-27F

<400> SEQUENCE: 1
agagtttgat cctggctcag                                            20

<210> SEQ ID NO 2
<211> LENGTH: 19
<212> TYPE: DNA
<213> ORGANISM: Artificial Sequence
<220> FEATURE:
<223> OTHER INFORMATION: universal primer for 16S rRNA for
      identification-1492R

<400> SEQUENCE: 2
ggttaccttg ttacgactt                                             19

```
<210> SEQ ID NO 3
<211> LENGTH: 20
<212> TYPE: DNA
<213> ORGANISM: Artificial Sequence
<220> FEATURE:
<223> OTHER INFORMATION: universal primer for 16S rRNA for
      identification-518R

<400> SEQUENCE: 3
ccagcagccg cggtaatacg                                              20

<210> SEQ ID NO 4
<211> LENGTH: 18
<212> TYPE: DNA
<213> ORGANISM: Artificial Sequence
<220> FEATURE:
<223> OTHER INFORMATION: universal primer for 16S rRNA for
      identification-805R

<400> SEQUENCE: 4
taccagggta tctaatcc                                                18

<210> SEQ ID NO 5
<211> LENGTH: 1508
<212> TYPE: DNA
<213> ORGANISM: Artificial Sequence
<220> FEATURE:
<223> OTHER INFORMATION: 16S rRNA sequence ofBacillus
      amyloliquefacienssubsp.
      plantarumCJ24-34

<400> SEQUENCE: 5
agagtttgat cctggctcag gacgaacgct ggcggcgtgc ctaatacatg caagtcgagc    60
ggacagatgg gagcttgctc cctgatgtta gcggcggacg ggtgagtaac acgtgggtaa   120
cctgcctgta agactgggat aactccggga aaccggggct aataccggat ggttgtctga   180
accgcatggt tcagacataa aaggtggctt cggctaccac ttacagatgg acccgcggcg   240
cattagctag ttggtgaggt aacggctcac caaggcgacg atgcgtagcc gacctgagag   300
ggtgatcggc cacactggga ctgagacacg gcccagactc ctacgggagg cagcagtagg   360
gaatcttccg caatggacga aagtctgacg agcaacgcc gcgtgagtga tgaaggtttt    420
cggatcgtaa agctctgttg ttagggaaga acaagtgccg ttcaaatagg gcggcacctt   480
gacggtacct aaccagaaag ccacggctaa ctacgtgcca gcagccgcgg taatacgtag   540
gtggcaagcg ttgtccggaa ttattgggcg taaagggctc gcaggcggtt tcttaagtct   600
gatgtgaaag cccccggctc aaccggggag ggtcattgga aactgggaa cttgagtgca    660 gaagaggaga gtggaattcc acgtgtagcg gtgaaatgcg tagagatgtg gaggaacacc   720
agtggcgaag gcgactctct ggtctgtaac tgacgctgag gagcgaaagc gtggggagcg   780
aacaggatta gataccctgg tagtccacgc cgtaaacgat gagtgctaag tgttaggggg   840
tttccgcccc ttagtgctgc agctaacgca ttaagcactc cgcctgggga gtacggtcgc   900
aagactgaaa ctcaaaggaa ttgacggggg cccgcacaag cggtggagca tgtggtttaa   960
ttcgaagcaa cgcgaagaac cttaccaggt cttgacatcc tctgacaatc ctagagatag  1020
gacgtcccct tcggggcag agtgacaggt ggtgcatggt tgtcgtcagc tcgtgtcgtg   1080
agatgttggg ttaagtcccg caacgagcgc aaccccttgat cttagttgcc agcattcagt  1140
tgggcactct aaggtgactg ccggtgacaa accggaggaa ggtggggatg acgtcaaatc   1200
atcatgcccc ttatgacctg gctacacac gtgctacaat ggacagaaca aagggcagcg   1260
```

```
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct ttatggagcc agccgccgaa ggtgggacag atgattgggg tgaagtcgta    1500
acaaggta                                                             1508
```